United States Patent [19]

Potter et al.

[11] Patent Number: 4,655,202

[45] Date of Patent: Apr. 7, 1987

[54] BANDAGES, COMPONENTS THEREOF AND USE

[75] Inventors: William D. Potter, Bishops Stortford; Sinan B. Kiamil, Harlow; Nicholas D. White, Bishops Stortford, all of United Kingdom

[73] Assignee: Smith and Nephew Associated Companies p.l.c., United Kingdom

[21] Appl. No.: 639,914

[22] Filed: Aug. 10, 1984

Related U.S. Application Data

[63] Continuation-in-part of Ser. No. 562,593, Oct. 19, 1983.

[30] Foreign Application Priority Data

Aug. 18, 1983 [GB] United Kingdom ............... 8322200

[51] Int. Cl.$^4$ ..................... A61F 5/04; C08F 122/10
[52] U.S. Cl. ..................................... 128/90; 524/413; 524/435; 524/418; 524/419; 526/320; 523/111
[58] Field of Search ............. 524/418, 419, 413, 435, 524/779, 785, 787; 523/105, 109, 111; 128/90, 92 A; 526/320

[56] References Cited

U.S. PATENT DOCUMENTS

| | | | |
|---|---|---|---|
| 4,286,586 | 9/1981 | Potts ................................. | 128/90 |
| 4,344,423 | 8/1982 | Evans et al. ....................... | 128/90 |
| 4,427,003 | 1/1984 | Fennimore et al. ............... | 523/111 |
| 4,435,540 | 3/1984 | Kishida et al. .................... | 524/785 |

FOREIGN PATENT DOCUMENTS 7499182 9/1974 Japan .
56-34453 4/1981 Japan .

OTHER PUBLICATIONS

Chem. Abstracts, vol. 95, entry 8444e.
Chem. Abstracts, vol. 82, entry 126134h.
Chem. Abstracts, vol. 85, entry 33722u.

*Primary Examiner*—Joseph L. Schofer
*Assistant Examiner*—Peter F. Kulkosky
*Attorney, Agent, or Firm*—Jacobs & Jacobs

[57] ABSTRACT

An orthopaedic bandage is described which comprises a support carrying a vinyl compound, which compound polymerizes when exposed to a water-activated vinyl polymerization catalyst. The vinyl compound is a hydrophilic prepolymer which contains more than one polymerizable vinyl group. This prepolymer is in association with at least one component of a water-activatable vinyl polymerization redox catalyst in solid form in a water pervious coating which is insoluble in the prepolymer. Encapsulation of one component of the catalyst system in a water pervious coating provides a storage stable bandage which is activated by immersion in water and gives a satisfactory working time for immobilizing a limb compared to use of an uncoated catalyst.

16 Claims, No Drawings

BANDAGES, COMPONENTS THEREOF AND USE

This is a continuation-in-part of application U.S. Ser. No. 562,593 filed 19th Oct. 1983 entitled "Bandages, Components Thereof and Use" and which application is incorporated herein by cross-reference.

The present invention relates to an orthopaedic bandage which hardens as a result of polymerisation of vinylic groups, components for use in such bandages and to the use of such bandages for immobilising parts of the body and to splints formed therefrom.

Traditionally, Plaster of Paris has been used in orthopaedic bandages or splinting bandages. However, in recent years there has been a tendency to seek lighter materials. One approach to providing such orthopaedic bandages has been to employ isocyanate containing compounds which polymerise on exposure to water and in doing so harden and set. Bandages of this kind are described in DT No. 2651089, GB No. 1578895, EPO No. 0057988 and PCT WO No. 81/00671. However isocyanates are highly reactive towards moisture and require complicated manufacturing and storage processes to prevent premature setting. An alternative approach to provide a lightweight synthetic splinting agent is to employ material which can polymerise on exposure to ultra violet light. Such systems are disclosed in GB No. 1407795, GB No. 1512553, U.S. Pat. No. 3881473 and U.S. Pat. No. 3985128 but such systems have not proved entirely satisfactory and require a light source which is not always convenient. A third approach which avoids the water sensitivity of the isocyanate system and does not require the light source of the ultra violet activatable system employs solid, water-soluble vinylic monomers which can be caused to polymerise and, in so doing, to harden and set. Bandages of this kind which employ vinylic polymerisation are described in GB No. 1592228, GB No. 2021128A, EP No. 008195, U.S. Pat. No. 3630194, U.S. Pat. No. 3968791, U.S. Pat. No. 4134397 and U.S. Pat. No. 4214578. Such bandages comprise a support carrying a cast-forming composition comprising a solid, water-soluble vinyl monomer which polymerises when exposed to a water-activated vinyl polymerisation catalyst, thereby causing the cast to set, some require disadvantageously elevated temperatures to cause setting. A related system is described in U.S. Pat. No. 3908644 but that required somewhat hazardous solvents to be employed for the catalyst system described. These various known vinylic orthopaedic bandages can suffer from problems pertaining to low strength, shelf life, difficulties in their application due to their being brittle, employing crystalline solids or volatile liquids, and the like.

Clearly, there is a need for a synthetic splinting system which can be employed without recourse to highly water sensitive materials such as isocyanate being present in the bandage, which does not require a light source to activate the system, which does not employ toxic solvents in order to activate the system, which can be activated at room temperature, which can produce a strong cast and which does not require comlicated packaging. This problem is solved by copending European Application No. 83302573 now published as European Application No. 0094222 and also as International Application No. 83/03973, Japanese Application No. 59-500751 and U.S. Ser. No. 562,593 the disclosure of which is incorporated herein by reference, and which provides an orthopaedic bandage which comprises a support carrying a vinyl compound, which compound polymerises when exposed to a water-activated vinyl polymerisation catalyst.

By using a vinyl compound a hydrophilic propolymer which contains not less than two polymerisable vinylic groups, a storage stable, readily activatable bandage can be produced which on exposure to a water activated polymerisation catalyst produces a cast of good strength.

A suitable catalyst is a redox catalyst comprising an oxidising component and a reducing component. For the sake of convenience it is preferred that at least one component is in association with the prepolymer prior to introducing water to the system and it is one of the very considerable advantages of the preferred bandages of U.S. Ser. No. 562593 that the catalyst is in association with the prepolymer so that the bandage need only be introduced to water (rather than a solution of the catalyst or a component thereof) in order to make it set. The bandages of containing the catalyst ab initio are storage stable.

The bandages of U.S. Ser. No. 562,593 are reactive once water-activated. Thus, preferably the orthopaedic bandage is wrapped around the member to be immobilised before the catalyst is brought into contact with the water.

It is one of the considerable advantages of these bandages that the cast may be produced by wetting the bandage once it has been positioned on the body. These bandages have relatively rapid set times.

However, conventional orthopaedic bandages are soaked in water prior to application, thus requiring relatively longer working times, and this application mode is desired in some areas of therapy. It is advantageous if such working times are however combined with a set time which is not excessively longer.

Orthopaedic bandages having the advantages of those of U.S. Ser. No. 562,593 with the relatively longer working times of a pre-soak bandage are now provided, by providing at least one component of the redox catalyst with a water-pervious coating.

The present invention provides an orthopaedic bandage which comprises a support carrying a vinyl compound, which compound polymerises when exposed to a water-activated vinyl polymerisation catalyst characterised in that the vinyl compound is a hydrophilic prepolymer which contains not less than two polymerisable vinylic groups and optionally said pre-polymer is in association with at least one component of a water-activatable vinyl polymerisation redox catalyst in solid form in a water pervious coating.

The present invention thus provides an orthopaedic bandage comprising a support carrying a vinyl compound which compound polymerises when exposed to a water-activated vinyl polymerisation catalyst characterised in that the vinyl compound is a hydrophilic prepolymer which contains more than one polymerisable vinyl group and said prepolymer is in association with at least one component of a water-activatable vinyl polymerisation redox catalyst in solid form in a water-pervious coating.

Any water pervious coating may be used to coat a catalyst component including coatings which permit passage of water by permeation, by being water soluble or by the presence of pores. Normally the polymers forming the water pervious coatings will be hydrophilic polymers. Preferred hydrophilic polymers are those which are swellable in water.

As is clear from the description hereinafter of the water-activatable catalysts used in the present invention, 'in association' includes the circumstances where the catalyst component(s), (at least one of) which is coated as defined, may be uniformly dispersed in the prepolymer or impregnated into the support. Preferably the catalyst component(s) are mixed in with the prepolymer thereby forming a uniform dispersion.

As is also clear from this description the invention thus also provides an orthopaedic bandage of the type hereinbefore defined, characterised in that said prepolymer is in association with a water-activatable polymerisation redox catalyst, at least one of the components of which is in solid form in a water-pervious coating. The catalyst will preferably be uniformly dispersed in the prepolymer.

'In solid form in a water-pervious coating' includes individual particles of the, one or each component of the redox catalyst so coated, and agglomerates of particles of the same or different component(s) of the catalyst so coated.

The prepolymer is in association with the oxidising agent or reducing agent, or preferably, both.

When the prepolymer is in association with both components, either or both may be in a water-pervious coating, and the reductant or the oxidant may be so coated.

The coated component(s) is/are often dispersed through the prepolymer in particulate form. The uncoated component when present may be dispersed through the prepolymer in particulate form or dispersed into the prepolymer or impregnated into the backing in solution with subsequent evaporation of solvent. Clearly, in order to provide a coating for the catalyst component(s), the coating material must not be soluble in or dispersible by any other component of the bandage, for example any residual formulation solvents.

Suitable oxidising agents include ammonium persulphate, potassium or sodium persulphate, hydrogen peroxide, ferric chloride and copper salts.

Copper (II) salts also act as catalyst promoters, and catalysts containing such promoters are preferred. Suitable copper salts can include readily water-soluble salts such as hydrated copper sulphate ($CuSO_4 5H_2O$). The number of copper ions and therefore the rate of the polymerisation of prepolymer will depend to some extent on the amount present in the prepolymer and the water solubility of the copper salt. To obtain a polymerisation rate suitable for setting orthopaedic bandages it is preferred that the copper salt has an adequate (slight) solubility in water. A preferred copper salt of this type is cupric acetylacetonate also referred to as copper (II) acetylacetonate.

Suitable reducing agents include ferrous sulphate, sodium sulphite, sodium dithioite, sodium thiosulphate, ferrous chloride, sodium formaldehyde sulphoxylate, sodium metabisulphite and the like. Soluble metabisulphite salts such as the sodium or potassium or ammonium salts are preferred reducing agents of which the sodium salt is most preferred. It has proved particularly advantageous to provide these salts as the coated component.

The coated catalyst component is generally in particulate form, the uncoated particles suitably having a mean particle size of 10 to 500$\mu$, favourably 50 to 200$\mu$, in particular about 100$\mu$.

The particles, or agglomerates thereof are in general essentially completely coated as defined, usually over in excess of 95% of their surface, preferably over in excess in 99%.

Suitable coating materials include polymers derived from those suitably functionalised vinyl group containing compounds described hereinafter as favoured for the bandage prepolymers.

Thus, favoured polymers include those of hydroxyethyl acrylic esters, such as hydroxyethyl acrylate and methacrylate, preferably 2-hydroxyethyl methacrylate.

It is believed that the working time of the bandages of the present invention may be increased by incorporating more hydrophobic copolymer monomer units into the coating polymer, whilst retaining the overall hydrobilic nature of the polymer which helps to make it water-pervious.

Thus, suitable coating materials also include copolymers of the foregoing functionalised vinylic group containing monomers with the following: acrylic and methacrylic acids esterified by alkyl such as ethyl, aryl such as phenyl, aralkyl such as phenethyl; and styrene.

In general it will not be desired to shorten the working time, but it is believed that this may be effected using as coating materials copolymers of the foregoing functionalised monomers with more hydrophilic monomers such as acrylic and methacrylic acids and vinylpyrrolidone.

Working times may also be adjusted to some extent by routine trail-and-error adjustment of coating thicknesses. It is however believed that increasing the coating thickness above about 35$\mu$ has little effect on the working time at that thickness, for a given coating material.

Suitable coating thicknesses lie in the range of 5 to 35$\mu$, favourably 15 to 30$\mu$, in particular about 25$\mu$.

Suitable weights of coating material to give a given coating thickness on a given weight of catalyst component will be readily calculable by the skilled man on the basis of component mean particle size and routinely available density data. By way of example equal weights of polyhydroxyethyl methacrylate and sodium metabisulphite (mean particle size 100$\mu$) give a coating of mean thickness of about 25$\mu$.

In general suitable weight ratios of catalyst component to coating component lie in the range of 99:1 to 1:9, favourably 10:1 to 1:3, in particular about 1:1.

A preferred redox polymerisation catalyst comprises a mixture of cupric acetylacetonate, and sodium metabisulphite, coated with polyhydroxyethyl methacrylate, and metabisuphite having a mean particle size of about 100$\mu$ and a mean coating thickness of about 25$\mu$. The ratio of sodium metabisulphite to cupric acetylacetonate in the catalyst mixture can be suitably from 1000 to 1, more usually from 250 to 1, for example 200 to 1 or 50 to 1.

The amount of catalyst used in the polymerisation process, eg in association with the prepolymer, is suitably 0.1% to 10% by weight and preferably 0.2 to approximately 6%, eg 0.2 to 4% by weight of the prepolymer.

In another aspect, the present invention provides a water-activatable vinyl polymerisation redox catalyst, at least one component of which is in solid form in a water-pervious coating.

Preferred catalysts of this type include those so described hereinbefore for the orthopaedic bandages of the present invention.

In a further aspect the invention provides a component, in solid form in a water-permeable coating, of a water-activatable vinyl polymerisation redox catalyst.

Preferred components and coatings of this type include those so described hereinbefore for the orthopaedic bandages of the present invention.

The prepolymer when exposed to a water-activatable vinyl polymerisation catalyst and water will polymerise to form a hard material, that is it will set.

Therefore the present invention in a still further aspect provides a novel cast-forming, water curable composition comprising at least one component of a water-activatable vinyl polymerisation redox catalyst in solid form in a water-pervious coating, in association with a polymerisable hydrophilic prepolymer which contains not less than two polymerisable vinyl groups. (Favoured prepolymers are hereinafter described.)

Inert materials may be incorporated into the prepolymer mixture. These materials include powdered fillers such as alumina, sodium aluminium silicates (such as Zeolex, available from Zeofin), china clay, powdered molecular seive, aluminium silicate, talc, plaster of paris, calcium phosphate, calcium carbonate, ground glass, silicas and titanium dioxide and fibrous fillers, for example glass fibres and colouring agents. A suitable alumina filter is G 5438, available from Ransden Ltd.

It is believed that the working time of the bandages of the present invention may be increased by the choice of less hydrophilic fillers, such as calcium carbonate and alumina.

Prepolymer is used herein in its conventional sense to mean an oligomer (that is a material intermediate between the monomer or monomers and the final polymer; as is understood in the polymer art such materials are of relatively low molecular weight compared to the final polymer but exclude monomers).

Preferred prepolymers are viscous liquids since bandages employing such materials have been found to have better unrolling and setting properties than those employing solid materials (especially after storage).

The prepolymer for use in orthopaedic bandages of this invention is most suitably a low molecular weight material which is capable of being polymerised further. Suitable low molecular weights include number average molecular weights in the range 400 to 24,000, preferably 600 to 20,000, in particular 1,100 to 16,000.

The prepolymer must, of course, be one which is sufficiently attractive to water to be itself capable of polymerising (causing the cast to set) when exposed to a vinyl polymerisation catalyst which is activated by introduction of water and, therefore, in this sense the prepolymer is a hydrophilic prepolymer. Hydrophilic prepolymers have proved surprisingly advantageous in producing a bandage which wets through uniformly and produces a good quality cast.

Normally the hydrophilic prepolymer employed will be one which swells on addition of water (that is if the dry prepolymer is exposed to water it takes up water but does not dissolve therein). It has been found that such hydrophilic prepolymers give a rapid setting time to the bandage and also have been found to give improved cast strength to the set bandage. Preferred hydrophilic prepolymers are capable of absorbing at least 5% and more aptly at least 10% by weight of their own weight of water. A simple method of determining how much a prepolymer swells on addition of water is to determine the increase in weight of a thin film (eg 25 microns) of dry prepolymer supported on a glass slide when introduced to an atmosphere saturated in moisture vapour until equilibrium is reached. It has been found to be particulary advantageous to employ a hydrophilic prepolymer which is dispersible in water (that is infinitely mixable with water but does not dissolve).

The prepolymer contains not less than two vinyl groups per molecule, (average functionality when, as is normal, the prepolymer is a mixture of compounds) and preferably the prepolymer contains not less than 3 vinyl groups per molecule. It has been found that particularly good cast strength can be achieved by employing hydrophilic prepolymers containing not less than 3 vinylic groups per molecule. Generally the prepolymer contains not more than 6 vinyl groups per molecule and suitably contains not more than 4 vinyl groups per molecule. The preferred prepolymer employed in this invention contains 3 vinyl groups (average functionality).

Normally the vinylic group will be in a terminal or pendant position of the prepolymer molecule as this has been found to allow ready polymerisation of the prepolymer.

Favourably the vinyl group is selected from an acrylic or methacrylic group. Thus, from the foregoing, it will be appreciated that highly favoured bandages of this invention comprise a hydrophilic prepolymer having not less than 2 acrylate or methacrylate groups per molecule in association with which is a water activatable acrylic polymerisation catalyst. Although acrylate or methacrylate esters are preferred, analogous amides are also apt. Perferably the vinyl group is an acrylate or methacrylate ester group and more preferably the vinyl group is a methacrylate ester group.

From the foregoing it is clear that favoured bandages of this invention will utilize a hydrophilic prepolymer which contains not less than 2 and preferably not less than 3 acrylate or methacrylate groups. Preferred preopolymers for use in the bandage of this invention contain 3 acrylic or methacrylic ester groups per molecule.

We have found, as discussed further hereinafter, that inclusion within the hydrophilic prepolymer employed in the bandage of this invention of a tertiary amino group has considerable surprising advantages. Thus, for example, use of a prepolymer containing a tertiary amino group aids in producing a bandage with favourable storage stability and favourable setting time.

Bandages employing prepolymers of the type hereinbefore described which also contain a tertiary amino form an especially favoured aspect of this invention. The most apt tertiary amino groups for inclusion in the molecule are pendant diloweralkylaminoloweralkyl groups (in which lower alkyl has upt to six carbon atoms and more suitably up to 3 carbon atoms) of which dimethylaminoloweralkyl groups are most suitable and of which the dimethylaminoethyl group is preferred. Such amino groups may be incorporated into the prepolymer by having employed an appropriate alkanol, for example dimethylaminoethanol, as precursor.

We have also found, as discussed further hereinafter, that inclusion of polyethylene oxide residues (for example 6 to 40% by weight) aids in producing prepolymers which are particularly suitable for use in the bandages of this invention.

Additionally we have found, as discussed further hereinafter, that the favoured prepolymers for use in the bandages of this invention employ vinylic groups derived from acryloyloxyloweralkoxy or methacryloxyloweralkoxy groups of which the methacryloyloxyethyloxy group is preferred.

Also, as described hereinafter, the bandage of this invention most suitably employs a prepolymer derived from an aliphatic isocyanate having an isocyanate functionality of not less than 2 and preferably an isocyanate functionality of 2.5 to 3.

The prepolymers employed in this invention are normally prepared by the condensation of smaller molecules which containing mutually reactive functional groups, for example alcohols or amines may be condensed with isocyanates or acid halides. In order to ensure that the prepolymer has the desired number of vinyl groups it is normal that at least one of the condensing molecules is polyfunctional, for example a polyisocyanate may be condensed with a vinyl compound which is suitably functionalised, for example with a hydroxy group so that it is an alcohol, or alternatively a polyol may be reacted with a vinyl compound which is suitably functionalised, for example, in the form of an acid chloride or which is functionalised in a way which provides it with an isocyanate group. We prefer to prepare prepolymers for use in this invention by condensing an isocyanate containing molecule with a hydroxyl containing molecule and we have found it most convenient to employ the hydroxyl containing molecule as the source of the vinylic group. However, as will be apparent hereinafter, considerable latitude is allowed the skilled worker in selecting the components to bring together to form the prepolymer with the desired properties.

The prepolymer used in this invention will be hydrophilic. The hydrophilic property is most aptly obtained by including within the prepolymer groups which will increase its attractiveness to water. Suitable groups for this purpose include polyoxyalkylene groups, salted amino groups, hydroxyl groups and salted carboxyl groups. The group we find most suitable for inclusion in the molecule are polyoxyalkylene groups, particularly those containing high proportions of polyoxyethylene residues such as those derived from polyethylene glycol. The use of such moieties is considered furthere hereinafter.

The prepolymers employed in this invention can have the hydrophilic groups included within its structure by condensing together several species in one reaction (for example a polyisocyanate may be reacted with a polyethylene glycol and a vinyl compound containing a hydroxyl group in the same reaction) or the hdyrophilic groups can already be present in one of the species (for example a polyisocyanate may be reacted with a vinyl compound which contains hydrophilic moieties, for example one in which polyethylene glycol has been condensed onto a hydroxyl group of the vinyl compound). Various apt ways of ensuring the presence of the required hydrophilic groups are described hereinafter.

As previously indicated, the hydrophilic prepolymer can be one derived from the reaction between a suitably functionalised vinyl group containing compound and an organic compound having a functionality of not less than 2. It will be appreciated that references therein to numbers of groups per molecule and functionality relate to average numbers and functionalities.

'Suitably functionalised' of course means that the vinyl group containing compound contains a groups suitable for reaction with the polyfunctional organic compound.

The hydrophilic nature of the prepolymer may be conferred, at least in part, by hydrophilic groups originally present or derived from the vinyl group containing compound.

In general, the more hydrophilic groups in the prepolymer molecule, the more hydrophilic the prepolymer will be. Suitable hydrophilic groups containing vinyl compounds include ethylene oxide adducts. Such compounds can have from 1 to 20 oxyethylene groups per molecule and preferably from 1 to 10 oxyethylene groups per molecule. Suitable hydrophilic groups containing vinyl compounds of this type include the acrylate and methacrylate esters of ethylene glycol and polyethylene glycol.

An apt hydrophilic group containing vinyl compound is a poyethylene glycol monomethacrylate with an average of five oxyethylene groups per molecule and an average molecular weight of from 300 to 400. A compound of this type is known as Sipomer PEG MM made by Alcolac Chemicals Inc. Sipomer PEG MM has an average molecular weight of about 364. Another compound is known as PE 350 made by Kanematsu Gosho and available from R. W. Unwin.

The terminal hydroxyl groups provide suitable functionalisation for reaction with a polyfunctional organic compound (such as a polyisocyanate which is reactive towards hydroxyl groups). This is further discussed hereinafter.

However it is not necessary for the vinylic component to contain hydrophilic groups since these may be derived from the other precursor of the prepolymer.

Preferred bandages of the present invention use a prepolymer derived from a suitably functionalised vinyl group containing compound, a suitably functionalised hydrophilic group containing compound and an organic compound having a functionality of more than one capable of reacting with the aforementioned compounds.

The resultant prepolymer thus has a vinylic component, a hydrophilic component and a linking component (derived from the organic compound).

Such polymers are preferred since separation of the vinyl group and the hydrophilic group or groups into two different components generally results in a harder setting prepolymer than one containing a hydrophilic vinyl component.

Suitable vinylic components include those containing acrylic and methacrylic groups, as described hereinbefore. Favourably such vinylic components are derived from suitably functionalised acrylamides and methacrylamides and preferably from acrylate and methacrylate esters. Preferred vinylic components include those derived from suitably functionalised alkyl esters of acrylic and methacrylic acid.

Suitable functionalised groups include hydroxyl and amino where the formative reaction is with a polyfunctional organic compound which is reactive towards hydroxyl and amino groups. This is further discussed hereinafter. The preferred functionality group is the hydroxyl group.

Favoured vinylic components thus include those of the general formula:

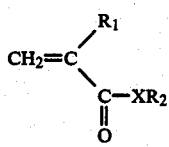

wherein $R_1$ is a hydrogen or methyl; X is O or NH and $R_2$ is a group which will be O- or N- substituted in the prepolymer and selected from: hydroxyalkyl, hydroxyaryl, aminoaryl and aminoalkyl and aminoaryl optionally substituted at the nitrogen by an alkyl. Apt alkyl groups contain not more than 6 carbon atoms. Favoured alkyl groups contain 2 or 3 carbon atoms.

Favoured functionalised vinyl compounds include hydroxyethyl esters so that particularly favoured vinylic components include acryloyloxy-ethoxy and methacryloyloxy-ethoxy groups.

A preferred compound is 2-hydroxyethyl methacrylate, so that preferred vinylic components include the methacryloyloxyethoxy group. Generally when employed this component comprises 6 to 45% wt/wt of the prepolymer, more usually 16 to 40% wt/wt of the prepolymer and preferably 17 to 34% of the prepolymer. Analogous vinylic components will generally be employed on an equivalent wt/wt basis.

The hydrophilic component is preferably a polyalkylene oxide such as polyethylene oxide or a polyethylene oxide containing polymer. These may be homo- or co- (including block co-)-polymers of polyethylene oxide and other alkylene oxides such as propylene oxide.

Suitable examples of the hydrophilic component include derivatives of polyalkylene glycols and polyalkoxylated mono- and poly-ols and polyalkyloxylated mono- and poly-amines, in particular such compounds based on homo- or co- (including block co-) polymers of ethylene oxide or propylene oxide. Hydrophilic components derived from polyethylene glycols or polyethylene glycol mono-ethers are preferred of which those derived from polyethylene glycols are particularly preferred.

The hydrophilic compound suitably may have a functionality of 1 to 5, favourably 2 to 3 and preferably 2.

The ethylene oxide content of the hydrophilic component is desirably at least 50% by weight and preferably at least 80% by weight of the hydrophilic component.

The hydrophilic compound is preferably dispersible in water.

Favoured examples of the hydrophilic compound include polyalkylene glycols and glycol monoethers, in particular such glycols and ethers based on homo- or co- (including block co-) -polymers of ethylene oxide and propylene oxide. Polyethylene glycols and glycol monoethers are preferred and polyethylene glycols are particularly preferred.

Favoured hydrophilic components thus include those of the general formula:

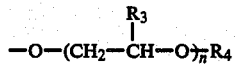

where n is 10 to 225; $R_3$ is hydrogen or methyl, $R_4$ is a bond, hydrogen or lower alkyl; and $R_3$ may be the same or different in adjacent repeat units with the proviso that in at least 50% and preferably in at least 80% of units $R_3$ is hydrogen.

The value of n referred to herein is of course a number average value for the hydrophilic compound and its corresponding component in the prepolymer.

n is most suitably 20 to 140 and is preferably 30 to 40.

Most desirably in all units $R_3$ is hydrogen since, as stated hereinbefore polyethylene oxide based hydrophilic components are preferred.

Suitable polyethylene oxide and/or polypropylene oxide based hydrophilic compounds include polyethylene glycols, for example PEG 400 to PEG 6000, polyethylene glycol-polypropylene glycol block copolymers, for example L64 and polyglycol 75W270 available from British Petroleum, polyethoxylated mono-ols such as polyethylene glycol monomethyl ether, ethoxylated polyols such as ethoxylated glycerol, for example PEG 1256 available from Imperial Chemical Industries Ltd and ethoxylated trimethlolpropanes available from Pechiney Eugene Kuhlman and ethoxylated amines such as Crodamets and Dicrodamets available from Croda Chemicals Limited. PEG 1500 is particularly suitablem for example as available from British Petroleum (Hythe Chemicals Ltd.).

Polyethylene glycols and the prepolymers derived from them are preferred.

The hydrophilic properties of such prepolymers will often depend on the amount and type of the polyethylene glycol from which the prepolymer is derived. The water sensitivity of the prepolymer will usually be proportional to the number of oxyethylene groups in the polyethylene glycol. Thus it is possible to obtain prepolymers with differing hydrophilic properties by varying the proportion and type of the polyethylene glycol used to form the prepolymer.

The hydrophilicity of prepolymers used in the invention is important for a number of reasons. For example it is a factor in determining the rate of the polymerisation of the prepolymer in the presence of the water-activated vinyl polymerisation catalyst. The more hydrophilic groups present in the prepolymer, the more effective the catalyst has been found to be subject to any contrary effect such as the introduction of crystallinity caused by using a polyethylene oxide of high molecular weight.

For this reason it is preferred that the hydrophilic prepolymers of this invention are hydrophilic to the extent that they are water-swellable and capable of absorbing at least 5% w/w and preferably at least 10% w/w of water, as stated hereinbefore.

Other physical properties, such as physical form, also depend to some extent on the percentage amount of the component derived from polyethylene glycol in the prepolymer and the type of glycol used.

The physical form of the prepolymer is also a factor in determining efficiency of catalyst activation where a water-activated catalyst is used, the efficiency of catalysis where a catalyst is used and the rate of polymerisation of the prepolymer. Ease of application and adhesion to the bandage support, and self-adhesion and interlayer polymerisation to form a cast or sprint discussed hereinafter have been found to be largerly determined by the physical form of the polymer.

For these reasons, it is preferred that the prepolymer is a viscous liquid.

Favoured prepolymers may be obtained by optimisation of the type of glycol used and the proportion of the corresponding component in the prepolymer.

For such prepolymers, apt polyethylene oxide derivatives include the polyethylene glycols having a molecular weight of between 400 and 6000, and favourably of between 600 and 6000. The preferred polyethylene oxide containing compound is a polyethylene glycol having a molecular weight of 1500.

The polyethylene oxide component of the preopolymer is favourably 6 to 40% by weight, preferably 10 to 30% by weight of the prepolymer.

Compared with prepolymers containing a hydrophilic, e.g. ethoxylated vinyl component, prepolymers of the foregoing type are preferred since separation of the vinyl group and the polyethylene oxide into two different components results in a prepolymer which sets harder than if the two moieties are in the same component.

Although the discussion of prepolymer optimisation above has been in terms of optimisation of the type and proportion of polyethylene glycol, similar considerations apply to other hydrophilic compounds furnishing hydrophilic components in the prepolymer.

Thus for example polyoxyethylene-polyoxypropylene diol block copolymers are also apt but less preferred. Suitable polyoxyethylene-polyoxypropylene block copolymers have a molecular weight of between 1500 and 3000 and a polyoxyethylene content of 40 to 60%.

Terminal hydroxyl or amino groups in the hydrophilic compound provide suitable functionalisation for reaction with a polyfunctional organic compound which is reactive towards hydroxyl or amine groups.

The prepolymer contains linkages which will be stable during a vinyl polymerisation reaction. Suitable linkages include ester, ether and amide linkages. Preferably, the prepolymer contains urethane linkages. Such prepolymers containing urethane linkages can be derived from the reaction between an organic isocyanate having a functionality of not less than two and a suitable functionalised vinyl compound (as described above). Such prepolymers may also be derived from a hydrophilic group containing compound (as described above).

Suitable organic isocyanates include aliphatic (including alicyclic) isocyanates and aromatic isocyanates having a functionality of not less than 2. Most suitably the isocyanate has a functionality of 2.5 to 3 for example 3. Generally the isocyanate has a functionality of not more than 6 and more usually not more than 5. Preferred isocyanates have been found to be aliphatic isocyanates. Thus aliphatic isocyanates having 3 isocyanate groups per molecule are particularly suitable.

Suitable aromatic and aliphatic isocyanates include any of those generally known in polyurethane chemistry, for example as described in 'Polyurethanes: Chemistry and Technology Part 1 Chemistry' Interscience Publishers (1962) or Kirk-Othmer Encyclopedia of Chemical Technology, 3rd. Ed., John Wiley & Sons, 1981, Vol. 13, p. 789-818.

An apt alicyclic isocyanate which has a functionality of 2 is 1,1'methylene-bis(4-isocyanate-cyclohexane) which is known as Desmodur W (available from Bayer (UK) Ltd.).

Apt aromatic isocyanates include 1,1',1"'-methylidyne tris(4-isocyanato-phenyl) which is known as Desmodur R and Desmodur L both having a functionality of 3 and which are available from Bayer (UK) Ltd.

Preferred organic isocyanates are aliphatic isocyanates. A suitable aliphatic isocyanate is a polyfunctional isocyanate derived from hexamethylene diisocyanate having a functionality of 2.5 to 3. A favoured aliphatic isocyanate of this type is known as Desmodur N 100 available from Bayer (UK) Limited.

Generally the isocyanate accounts for 10 to 60% wt of the prepolymer, more suitably 15 to 55% wt of the prepolymer and preferably 30 to 50% wt. of the prepolymer.

Apt prepolymers for use in orthopaedic bandages of this invention are derived from the reaction between an aliphatic isocyanate having a functionality of not less than two and a mixture of the monomethacrylate (or monoacrylate) esters of ethylene glycol and polyethylene glycol.

Other preferred prepolymers are derived from the reaction between an aliphatic isocyanate having a functionality of not less than two, an arcylate or methacrylate containing compound and polyethylene glycol.

A favoured prepolymer is derived from the reaction between an aliphatic isocyanate having a functionality of 2.5 to 3, for example Desmodur N 100, 2-hydroxyethyl methacrylate and a polyethylene glycol monomethacrylate. having an average of five oxyethylene groups per molecule, for example PE 350 or Sipomer PEG MM.

A more favoured prepolymer is derived from the reaction between an aliphatic isocyanate having a functionality of 2.5 to 3, for example Desmodur N 100, 2-hydroxyethyl methacrylate and a polyethylene glycol such as PEG 6000, or yet more favourably PEG 1500.

It is preferred, in order to avoid any potential problems of toxicity, that the prepolymers used in the present invention are essentially free of monomer. It is one of the considerable advantages of the bandages of this invention that they do not require the presence of a monomeric vinyl compound with the potential toxicity problems connected therewith.

It has also been found that prepolymers derived from the reaction between at least a linking compound having a functionality of more than one, a suitably functionalised vinyl group containing compound, a hydrophilic group containing compound and a suitably functionalised accelerator are particularly useful in bandages of this invention.

An accelerator, in this context, is a substance which increases the setting rate of the orthopaedic bandage. Preferred accelerators are tertiary amines such as N,N-dimethylethanolamine.

Functionalised accelerators may be represented by the general formula:

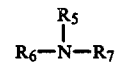

wherein $R_5$, $R_6$ and $R_7$ are each independently a hydrocarbyl radical or any two together are a hydrocarbadinyl diradical, and all three together contain at least one hydroxyl or NH $R_8$ group where $R_8$ is hydrogen or a hydrocarbyl radical.

$R_4$ to $R_8$ may be further substituted by any substituent compatible with the function of the compound.

Each or $R_4$ to $R_8$ may be an alkyl, cycloalkyl or aryl radical or a monovalent radical comprising alkyl, cycloalkyl or aryl components, for example aralkyl; or any two of $R_4$, $R_5$ and $R_6$ together may be polymethylene.

Thus each may be a straight chain alkyl group, preferably $C_{1-4}$alkyl, $C_{5-8}$cycloalkyl or phenyl; or any two as above together may be $C_{4-5}$polymethylene.

Preferably $R_4$ is hydroxy $C_{1-4}$alkyl in particular 2-hydroxyethyl. Preferably $R_5$ is methyl. Preferably $R_6$ is methyl.

Most aptly the amine is included in the range $1 \times 10^{-5}$ to $1 \times 10^{-3}$ mole $Ng^{-1}$, more aptly $3 \times 10^{-5}$ to $6 \times 10^{-4}$ mole $Ng^{-1}$ and preferably $7 \times 10^{-5}$ to $4 \times 10^{-4}$ mole $Ng^{-1}$.

It has been found to be advantageous that where a cast is required which is white in colour, that addition to the prepolymer of an amount of an organic polyacid or a salt thereof provides a white cast with better surface characteristics. Favoured organic polyacids include those containing 2 or 3 carboxyl groups and 1, 2 or 3 hydroxyl groups. Particularly favoured organic polyacids include tartaric acid and citric acid and salts thereof which will not interfere with the polymerisation of the prepolymer. The amount of acid used will vary depending upon the acid used. For tartaric acid the amount used is suitably from 0.01 to 1 g and preferably 0.05 to 0.5 g for example 0.1 g, for each 50 g of prepolymer. For citric acid the amount used is suitably from 0.5 to 5 g and preferably 1 to 2 g, for each 50 g of prepolymer. Tartaric acid and its salts are particularly preferred. Salts may be employed but generally it is more effective to employ the acid. Bandages employing such acids form a favoured aspect of this invention.

Desirably, in orthopaedic bandages of the present invention, the prepolymer is in association with a polymerisation inhibitor to prevent premature polymerisation of the prepolymer during its preparation and storage.

Suitable polymerisation inhibitors include vinyl polymerisation inhibitors of the art. A favoured inhibitor for preventing polymerisation of prepolymers used in bandages of the present invention during their preparation and storage is phenothiazine. A favoured inhibitor for preventing premature polymerisation of such prepolymers during storage is methoxyhydroquinone.

The amount of polymerisation inhibitor in association with the prepolymer can suitably be 50 to 1000 ppm and preferably be 100 to 700 ppm of the prepolymer.

It desired, in orthopaedic bandages of the present invention, the prepolymer is in association with a plasticiser which enables the bandage to be more easily manipulated before it has set. A suitable plasticiser is silicone oil which may comprise approximately 10% w/w of the bandage.

Redox catalyst components for use in orthopaedic bandages of the present invention may be prepared by any convenient conventional (particle) coating process, compatible with the coating material, such as spray coating or coacervation. Suitable methods for given materials are given in standard text-books of the art such as Microencapsulation: Processes and Application, J. E. Vandegaer (Ed.), ACS Symposium on Microencapsulation—Plenum Press, 1974.

However, the favoured polyhydroxyethyl acrylic ester coating materials of the present invention and their copolymers of the type hereinbefore described lend themselves particularly to polymerisation encapsulation. This process unexpectedly provides a solution to the problem of providing a coherent coating over the whole encapsulated material without any significant agglommeration of coated particles.

Thus, in a further aspect the present invention provides a process for the preparation of a redox catalyst component coated in a hydroxyethyl acrylic ester polymer or copolymer, which process comprises suspending the finely particulate component in a solution of a hydroxyethyl acrylic ester optionally together with a vinylic comonomer compatible therewith in a solvent which is not a solvent for the desired (co)polymer, and polymerising the ester optionally together with its vinylic comonomer about the component particles to form coated particles of the component or coated agglommerates thereof.

Suitable solvents will be readily apparent to the skilled man, or readily established by routine trial-and-error. However, by way of example, solvents such as ethyl acetate, dichloromethane and acetone are believed to be suitable.

Suitable reaction conditions are typified by those in the relevant Example hereinafter, and obvious equivalents thereof.

Prepolymers for use in orthopaedic bandages of the present invention may be prepared by reacting a linking compound having a functionality of more than one with a suitably functionalised vinyl group containing compound.

Clearly, 'suitably functionalised' where used herein means that the compound must contain a functional group which will react with the linking compound.

The reaction may take place by simply mixing the reaction components (ie the organic isocyanate and the vinyl group containing compound and, where appropriate, the accelerator and, where appropriate, the separate hydroxy group containing compound). A catalyst such as dibutyl tin dilaurate can then be added to the mixture to increase the rate of reaction (i.e. to speed up the formation of the prepolymer) and the reaction allowed to continue until the exotherm has subsided.

A polymerisation inhibitor as described above may also be added into the reaction mixture during the preparation of the prepolymer. Alternatively, the polymerisation inhibitor can be added to the prepolymer mixture prior to coating it on the support. Either way, the prepolymer is in association with the polymerisation inhibitor.

A plasticiser as described above may also be added into the reaction mixture during the preparation of the prepolymer. Alternatively, the plasticiser can be added to the prepolymer mixture prior to coating it on to the support.

Preferably the reaction takes place in a solvent such as dichloromethane, tetrahydrofuran and mixtures thereof and the like. The preferred solvent is dichloromethane. This is more convenient than reacting the reaction components together in the absence of a solvent and subsequently diluting the prepolymer with solvent.

The prepolymer may then be brought into association with one or more components of a vinyl polymerisation redox catalyst, at least one of which is in solid form in a water premeable coating.

Preferably, the or each coated catalyst component is in a finely divided state, for example a powder, and is uniformly dispersed into the prepolymer. Any uncoated catalyst component may alternatively be impregnated into the support before coating with the prepolymer. More preferably the copper acetylacetonate is employed in a solution (in eg dichloromethane) which is mixed into the prepolymer.

A polymerisation inhibitor to prevent premature polymerisation of the prepolymer during storage may also be mixed in with the prepolymer.

Similarly, the prepolymer may be brought into association with the plasticiser by mixing.

The prepolymer mixture (i.e. the prepolymer and any associated ingredients) shall be sufficiently fluid without requiring modification to be used in the orthopaedic bandages of this invention. One of the advantages of employing a viscous liquid prepolymer is that this desirable end is readily achieved. However solvent dispersions and hot melts can be used if desirable.

An orthopaedic bandage of the present invention comprises a vinyl group containing prepolymer as described above carried on a support. The support will normally be a flexible fabric. The flexible fabric will preferably have apertures of sufficient size to enable water to permeate the bandage and cause it to set. Suitable aperture sizes are 0.2 mm to 10 mm and preferably 0.5 mm to 5.0 mm (minimum dimension of aperture).

Suitable flexible fabrics can be woven, knitted or non-woven fabrics made of materials which are inert to the prepolymer. The support will generally be elongate, and favoured flexible fabric supports are those having a low lengthwise stretch and a high widthwise stretch as such properties give good conformability. A suitable low lengthwise stretch is less than 15%, preferably less than 10%, and in particular less than 5%. A suitable high widthwise stretch is greater than 20%, preferably greater than 50%, and in particular greater than 100%.

To achieve such stretch values, a favoured flexible fabric is a Raschel warp knitted fabric.

Suitable support materials include fibres or filaments of cellulose, polyester, polyamides, polyolefines and glass or mixtures thereof.

Suitable glass fibre fabrics are disclosed in, for example, U.S. Pat. Nos. 4134397, 3985128, 3882857, 3881673, 3793686, 3787272, 3686725, German Offenlegungsschrift No. 2651089 and British Pat. Nos. 1512553 and 1407795.

Favoured flexible fabric carriers include gauzes such as leno gauze and warp knitted polyester fabrics. A preferred warp knitted polyester fabric has between 4 to 400 apertures per square centimeter.

Suitable fabric weights for a given thickness depend on the fabric material, but in general suitable weights are in the range 50 to 300 gsm, preferably 100 to 200 gsm.

In another aspect, the present invention further provides a method for the preparation of an orthopaedic bandage which comprises coating or impregnating a support with a vinyl compound which compound polymerises when exposed to a water-activated polymerisation catalyst, characterised in that the vinyl compound is a prepolymer which contains more than one polymerisable vinyl group in association with at least one component of a water-activatable vinyl polymerisation redox catalyst in solid form in a water-permeable coating.

Any suitable coating means can be used to coat the flexible fabric including fixed doctor blade over flat bed, or roller and roller coating systems.

It is desirable that the prepolymer mixture during coating is protected from excessive moisture vapour. Suitable coating systems can be enclosed and can be conducted in an atmosphere free from excessive moisture vapour such as dry air, or inert gases for example carbon dioxide or nitrogen. However this is not normally necessary except in highly wet atmospheres since it is one of the considerable advantages of this invention that the materials are much more stable to water than previously employed systems such as polyurethanes.

In a preferred continuous process the prepolymer mixture in liquid form is coated on to a length of flexible fabric by means of a blade over flat bed and the coated fabric dried, if necessary. The coated fabric can then be split into suitable size strips and rolled up into bandages.

The amount of prepolymer on the fabric carried should be sufficient to ensure that the resultant cast has adequate strength. Suitable amounts have been found to be 50 to 500 g/m$^2$, preferably 100 to 350 g/m$^2$, for example 200 g/m$^2$, 250 g/m$^2$ or 300 g/m$^2$.

Preferably the bandages should be protected during storage from water and excessive moisture vapour to prevent a premature setting taking place, the bandages can be conventionally packaged in heat sealed waterproof pouches such as metal foil polyethylene laminate or polyethylene pouches. Again it is one of the considerable advantages of this invenition that it is possible to use simple procedures and packages such as using polyethylene pouches.

In use the bandages may be brought into contact with water and wrapped aound the injured part of the body. The setting bandage has a working time which is a time sufficient to allow the bandage to be positioned, and a set time which is the time taken for the cast to become rigid. Favoured working times are 2 minutes to 6 minutes and especially 3 minutes to 4 minutes. Favoured set times are 5 minutes to 30 minutes and especially 6 minutes to 15 minutes.

Set times may be extended by routine trial-and-error choice of coating materials and thicknesses for the coated catalyst component, and by routine choice of less hydrophilic fillers or their omission.

The present orthopaedic bandages may be soaked in water prior to application.

The present invention still further provides a method of forming a rigid orthopaedic cast for body members which comprises providing an orthopaedic bandage comprising a support carrying a vinyl compound which polymerises when exposed to a water-activated vinyl polymerisation redox catalyst; providing a water-activatable vinyl polymerisation catalyst; and wrapping the orthopaedic bandage around the member to be immobilised, characterised in that the vinyl compound is a prepolymer which contains not less than two polymerisable vinyl groups, in association with at least one component of the catalyst in solid form in a water-pervious coating.

Alternatively and less preferably the orthopaedic bandage is wrapped around the member to be immobilised before the catalyst is brought into contact with the water.

In such a case the water is suitably sprayed or sponged on to the bandage, for example by using a spray or a sponge or cloth.

The water may contain a wetting agent such as a surfactant or a lower alkanol such as isopropanol but it is preferred to use water without adding such agents.

It is a considerable advantage of the invention that the setting-off of the bandage may be accomplished by treatment with such a non-toxic agent as water.

For this aspect of the invention it has been found that it is advantageous that the bandage be sufficiently tacky to adhere to itself in the dry state so that moulding around a limb or other part of the body is simplified. It is one of the advantages of using a tacky prepolymer that such tacky bandages may be obtained. Thus favoured prepolymers for use in this invention are non-solid prepolymers (that is preferably viscous liquid prepolymers) since such prepolymers are more tacky than solid prepolymers.

The following Examples illustrate the invention. The following Descriptions illustrate the preparation of prepolymers for the invention.

DESCRIPTION 1

Preparation of Prepolymer

To a well stirred mixture of Desmodur N (329.7 g 1.74 mol —NCO, Bayer) and dibutyl tin dilaurate (1.1 g, BDH) a mixture of 2-hydroxyethyl methacrylate (181 g, total —OH 1.48 mol), PEG 6000 (66.8 g, total —OH 0.087 mol), N,N-dimethylethanolamine (14.69 g, 0.174 mol total —OH) and pheothiazine (0.3 g) was added dropwise over 1 hour. The reaction is exothermic and should be cooled in a water bath so that pot temperature does not exceed 60° to 70° C. Gas is evolved from the reation between isocyanate and water from the added reagents.

The reaction mixture is then heated with stirring to 70° C. for ½ hour and allowed to cool. Dry dichloromethane (200 ml) and Tinuven P (3 g, Ciba Geigy) are added and the mixture is stirred until homogenous the poured into a bottle and capped.

DESCRIPTION 2

Preparation of Hydrophilic prepolymer

The required amounts of Desmodur N100, (1.2 mol NCO), 2-hydroxymethyl methacrylate (0.8 mol) and polyethylene glycol monomethacrylate (0.4 mol OH) and polyethylene the required amounts were weighed into a wide neck jar. The reaction mixture was hand mixed until a clear solution was obtained (approximately 1 minute).

Dibutyl tin dilaurate catalyst was added to increase the reaction rate and the reaction allowed to continue with mixing until the reaction exotherm had subsided. (Approximately 5 to 10 minutes). The prepared prepolymer was then stored in the dark for approximately 24 hours.

DESCRIPTION 3

Preparation of Prepolymer

A mixture of an aliphatic isocyanate (384.6 g, Desmodur N 100), dibutyl tin dilaurate (1.4 g) and dry dichloromethane (210 ml) was warmed with stirring until the mixture was refluxing gently. To this mixture was added dropwise over 1 hour a mixture of 2-hydroxyethyl methacrylate (211.4 g), polyethylene glycol (77.9 g, molecular weight 6000, Breox PEG 8000), N,N-dimethylethanolamine (17.1 g) phenothiazine (0.3 g) and dry dichloromethane (210 ml). The reaction mixture was maintained at reflux temperature and stirred during the addition. The final mixture was heated to reflux temperature and stirred for a further hour. Tinuven P (3.4 g) was then added and the mixture stirred until homogenous. The mixture was then allowed to cool and poured into a glass jar and firmly stoppered.

DESCRIPTION 4

Prepolymers 4–24

Prepolymers were prepared using the method described in Description 3 but in which various components were changed on an equivalent mole for mole basis.

| Prepolymer | Isocyanate type | Vinyl Compound | Polyoxy-alkylene glycol | Accelerator |
| --- | --- | --- | --- | --- |
| 4 | Desmodur N 100 | Hydroxyethyl acrylate | PEG 6000 | N,N—dimethyl ethanolamine |
| 5 | Desmodur N 100 | Hydroxypropyl acrylate | PEG 6000 | N,N—dimethyl ethanolamine |
| 6 | Desmodur N 100 | Glycerol monomethyl-ether mono-methacrylate | PEG 6000 | N,N—dimethyl ethanolamine |
| 7 | Desmodur N 100 | Diallylamine | PEG 6000 | N,N—dimethyl ethanolamine |
| 8 | Desmodur R | Hydroxyethyl methacrylate | PEG 6000 | N,N—dimethyl ethanolamine |
| 9 | Desmodur L | Hydroxyethyl methacrylate | PEG 6000 | N,N—dimethyl ethanolamine |
| 10 | PAPI 135 | Hydroxyethyl methacrylate | PEG 6000 | N,N—dimethyl ethanolamine |
| 11 | Desmodur W | Hydroxyethyl methacrylate | PEG 6000 | N,N—dimethyl ethanolamine |
| 12 | Desmodur N 100 | Hydroxyethyl methacrylate | PEG 600 | N,N—dimethyl ethanolamine |
| 13 | Desmodur N 100 | Hydroxyethyl methacrylate | PEG 1500 | N,N—dimethyl ethanolamine |
| 14 | Desmodur N 100 | Hydroxyethyl methacrylate | Polypropylene glycol 1025 | N,N—dimethyl ethanolamine |
| 15 | Desmodur N 100 | Hydroxyethyl methacrylate | Pluronic L35 | N,N—dimethyl ethanolamine |
| 16 | Desmodur N 100 | Hydroxyethyl methacrylate | Pluronic L64 | N,N—dimethyl ethanolamine |
| 17 | Desmodur N 100 | Hydroxyethyl methacrylate | PEG 6000 | N,N—diethyl ethanolamine |
| 18 | Desmodur N 100 | Hydroxyethyl methacrylate | PEG 6000 | N—methyl piperidin-2-methanol |
| 19 | Desmodur N 100 | Hydroxyethyl methacrylate | PEG 6000 | N—methyl, N—2-hydroxy- |

-continued

| Prepolymer | Isocyanate type | Vinyl Compound | Polyoxy-alkylene glycol | Accelerator |
|---|---|---|---|---|
| 20 | Desmodur N 100 | Hydroxyethyl methacrylate | PEG monomethyl ether 1900 | ethyl analine N,N—dimethyl ethanolamine |
| 21 | MDI | Hydroxyethyl methacrylate | PEG 6000 | N,N—dimethyl ethanolamine |
| 22 | Desmodur N 100 | Hydroxyethyl Methacrylate | Breox 75 W/270 | N,N—dimethyl ethanolamine |
| 23 | Desmodur N 100 | Hydroxyethyl methacrylate | Breox 75 W/18000 | N,N—dimethyl ethanolamine |
| 24 | Isonate 143L | Hydroxyethyl methacrylate | PEG 6000 | N,N—dimethyl ethanolamine |

| | | |
|---|---|---|
| 25. | Desmodur N 100 | 1 mole NCO |
| | Hydroxyethyl methacrylate | .88 mole OH |
| | PEG 6000 | .05 mole OH |
| | 3-N,N—diethylamino-2-hydroxypropyl methacrylate | .1 mole OH |
| 26. | Desmodur N 100 | 1 mole NCO |
| | Hydroxyethyl methacrylate | .9 mole OH |
| | 2-Hydroxy-3-methacryloxy propyl trimethyl ammonium chloride | .1 mole OH |
| 27. | Desmodur N 100 | 1 mole NCO |
| | Hydroxyethyl methacrylate | .7 mole OH |
| | PEG 1500 | .1 mole OH |
| | Methyl diethanolamine | .2 mole OH |
| 28. | PEG 1500 dimethacrylate | |
| 29. | PEG 300 dimethacrylate | |
| 30. | Isonate 143L | 1 mole NCO |
| | Hydroxyethyl methacrylate | .79 mole OH |
| | Tween 80 | .11 mole OH |
| | N,N—dimethyl ethanolamine | .1 mole OH |

PEG 6000 used is Breox 8000
Pluronic L64 is a polyoxyethylene-polyoxypropylene diol block copolymer of molecular weight 2900
Pluronic L35 has a molecular weight of 1900
Desmodur N 100 is an aliphatic isocyanate of functionality 3.
Desmodur W is an alicyclic isocyanate of functionality 2
MDI is 4'4 diphenylmethane di-isocyanate
Breox 75 W 270 and Breox 75 W 1800 are PEG/PPG copolymers available from British Petroleum.
Isocyanate 143L is a modified MDI which is liquid at room temperature, available from Upjohn.
Desmodur L and R are aromatic isocyanates of functionality 3. Desmodur isocyanates are available from Bayer.
Tween 80 is a polyethoxylated sorbitan monolaurate of molecular weight 3800, PEG 1500 is polyethylene glycol molecular weight 1500 available from British Petroleum.
PAPI is phosgenated analine formaldehyde condensate isocyanate available from Upjohn.

DESCRIPTION 5

Prepolymers 25–31

Prepolymers (except prepolymers 28 and 29) were prepared using the method described in Description 3 but in which various components were changed as follows. Prepolymers 28 and 29 were prepared by the reaction of the glycol with two moles of acryloyl chloride.

| | | |
|---|---|---|
| 31. | Isonate 143 L | 1 mole NCO |
| | Hydroxyethyl methacrylate | .8 mole OH |
| | Ethoxylated glycerol mw 1256 | .1 mole OH |
| | N,N—dimethyl ethanolamine | .1 mole OH |
| 32. | Desmodur N 100 | 1.0 mole NCO |
| | Hydroxyethyl mathacrylate | .85 mole OH |
| | PEG 1500 | .1 mole OH |
| | N,N—dimethylethanolamine | .05 mole OH |

DESCRIPTION 6

Prepolymers 33 to 38

Preparation of Hydrophilic Prepolymers

The aliphatic isocyanate (Desmodur N100), 2-hydroxymethyl methacrylate and/or polyethylene glycol monomethacrylate (PE 350 or Sipomer PEG MM) in the required amounts were weighed into a wide neck jar. The reaction mixture was hand mixed until a clear solution was obtained (approximately 1 minute). Dibutyl tin dilaurate catalyst was added to increase the reaction rate and the reaction allowed to continue with mixing until the reaction exotherm had subsided. (Approximately 5 to 10 minutes). The prepared prepolymer was then stored in the dark for approximately 24 hours.

Prepolymers were prepared according to the method given above.

| Prepolymer No. | Desmodur N 100 (moles) | 2-HEMA (moles) | PE 350 (moles) | Sipomer PEG MM (moles) | Catalyst (g) |
|---|---|---|---|---|---|
| 33 | 0.1 | 0.30 | — | — | 0.15 |
| 34 | 0.05 | — | 0.15 | — | 0.19 |
| 35 | 0.05 | 0.10 | 0.05 | — | 0.12 |
| 36 | 0.05 | 0.075 | 0.075 | — | 0.13 |
| 37 | 0.10 | 0.20 | — | 0.10 | 0.20 |
| 38 | 0.40 | 0.80 | — | 0.40 | 0.80 |

DESCRIPTION 7

The following resins were prepared by the process described in Description 3 of European Patent Application No. 0094222, at page 47, from the designated components.

| Prepolymer 39 | | |
|---|---|---|
| Desmodur N 100 | 212.50 g | (1 mole NCO) |
| Hydroxyethyl methacrylate | 112.00 g | (0.85 mole OH) |
| PEG 1500 | 75.20 g | (0.1 mole OH) |
| N, N—dimethyl ethanolamine | 5.20 g | (0.05 mole OH) |
| Prepolymer 40 | | |
| Desmodur N 100 | 98.28 g | (1 mole NCO) |
| Hydroxyethyl methacrylate | 61.85 g | (0.875 mole OH) |
| PEG 1500 | 38.72 g | (0.10 mole OH) |
| N, N—dimethyl ethanolamine | 1.13 g | (0.025 mole OH) |
| Prepolymer 41 | | |
| Desmodur N 100 | 220.60 g | (1.2 moles NCO) |
| Hydroxyethyl methacrylate | 110.50 g | (0.85 moles OH) |
| PEG 1500 | 74.32 g | (0.05 mole OH) |
| Diethyl ethanolamine | 5.85 g | (0.05 mole OH) |
| The mole ratio of NCO:OH was 1.1:1. | | |
| Prepolymer 42 | | |
| Desmodur N 100 | 212.07 g | (1.125 moles NCO) |
| Hydroxyethyl methacrylate | 117.00 g | (0.9 mole OH) |
| PEG 1500 | 74.32 | (0.05 mole OH) |
| The mole ratio of NCO:OH was 1.03:1. | | |
| Prepolymer 43 | | |
| Desmodur N 100 | 224.2 g | (1.10 mole NCO) |
| Hydroxyethyl methacrylate | 112.9 g | (0.88 mole OH) |
| PEG 1500 | 77.7 g | (0.05 mole OH) |
| Dimethylaminopropylamine | 5.2 g | (0.08 mole OH) |
| The mole ratio of NCO:OH was 1.09:1. | | |

EXAMPLE 1

Encapsulation of sodium metabisulphite by poly 2-hydroxyethyl methacrylate

2-Hydroxyethyl methacrylate (50 g), ethyl acetate (500 ml) and 100μ sodium metabisulphite (50 g) were placed in a 1 l t resin flask fitted with an anchor stirrer and a reflux condenser. The flask was purged with nitrogen. The contents of the flask were stirred at a rate sufficient to keep the powder suspended. The flask was heated in a water bath to 55° C. and then disopropylperoxydicarbonate (0.4 ml, 40% soln) was added. The stirred mixture was allowed to react for 1½ hrs. A slight exotherm resulted. The temperature was then raised to 68° and the reaction continued for 4 hrs.

The reaction mixture was cooled and the solid was filtered off, washed with ethyl acetate (3×500 ml), and then dried in a vacuum oven at 65° for 1 hr.

Yield 81.73 g; 81%.

EXAMPLE 2

Preparation and Testing of a Bandage

The following mixture was prepared:
19 g acrylic splint resin (Prepolymer 1, Description 1);
0.5 ml 0.9% w/v copper acetylacetonate soln in $CH_2Cl_2$;
0.45 g Sylosiv $A_4$ (powdered molecular sieve, W. R. Grace);
0.9 g coated sodium metabisulphite (ex Example 1);
0.5 g tartaric acid;
5 g precipitated chalk;
was coated at about 250 gsm onto a knitted polyester fabric whose mass weight was about 100 gsm. The coated fabric was then rolled onto a core to give the splinting bandage.

The bandage was immersed in water and then wrapped around a former. A working time of about 1½ to 2 mins was observed prior to a slight exotherm and rapid setting.

Any prepolymer of Description 1 may be used analogously in the preparation of bandages with similar properties.

EXAMPLE 3

Preparation and Testing of a Bandage

The following mixture was prepared:
40 g acrylic splint resin (Prepolymer 2, Description 1)
2 g coated sodium metabisulphite (as in Example 1)
0.01 g copper acetylacetonate
6 g Sylosiv $A_4$
6 g alumina
0.12 g tartaric acid The resin and coated sodium metabisulphate were mixed together in a mixing vessel. The copper acetylacetonate was added and mixed with the resin and catalyst.

The final mixture was coated at about 240 gsm onto a knitted polyester fabric whose mass weight per unit area was 100 gsm. The coated fabric was then rolled onto a core to give the splinting bandage.

The bandage was immersed in water and then wrapped around a former. A working time of 1 minute 40 seconds was observed prior to a slight exotherm and rapid setting.

EXAMPLES 4–9

Preparation and Testing of Bandages

Similar bandages to those described in Example were made from the following resins at various mass weight per unit area and had the following working times:

| Example | Resin | Mass per unit area on support (gsm) | Working time (minutes) |
|---|---|---|---|
| 4 | Prepolymer 43 | 260 | 1.5 |
| 5 | Prepolymer 42 | 257 | 3.0 |
| 6 | Prepolymer 40 | 439 | 1.3 |
| 7 | Prepolymer 43 | 336 | 1.5 |
| 8 | Prepolymer 42 | 338 | 2.5 |
| 9 | Prepolymer 41 | 314 | 3.5 |

EXAMPLE 10

Encapsulation of Cupric Sulphate by Poly 2-hydroxyethyl methacrylate

Copper sulphate (53 g) and ethyl acetate (725 ml) were placed in a 2 liter resin flask fitted with an anchor stirrer and a reflux condenser. The suspension was stirred for 1 hour at a temperature of 50° C. 2-Hydroxyethyl methacrylate (53 g) were added and the mixture stirred for a further 10 minutes. The flask was then purged with nitrogen. The catalyst of diisopropylperoxydicarbonate (0.41 ml, 40% w/v in dibutylmaleate) was added. The suspension was stirred for a further 6 hours under a nitrogen blanket at 70° C. The reaction mixture was then cooled to room temperature, about 20° C., and stirred for a further 24 hours.

The solid material was filtered off, washed with ethyl acetate (3×500 ml) and then dried in a vacuum oven at 80° C. for 1 hour.

Yield 84.6 g; 80%.

What is claimed is:

1. An orthopaedic bandage which comprises a support carrying a vinyl compound which compound polymerises when exposed to a water activated vinyl polymerization catalyst in which the vinyl compound is a hydrophilic prepolymer which contains more than one polymerizable vinyl group and said prepolymer is in association with at least one component of a water-activatable vinyl polymerization redox catalyst in a solid particulate form in a water pervious coating in which the particles have an uncoated size of from 10 to 500 μm and in which the water pervious coating is present over in excess of 95% of the particle surface and in which the weight ratio of catalyst to coating is 99:1 to 1:9 and in which the coating is insoluble in the prepolymer.

2. A bandage according to claim 1 in which the water-pervious coating is from 5 to 35 μm thick.

3. A bandage according to claim 1 in which the weight ratio of the redox catalyst component to the water-pervious coating is 10:1 to 1:3.

4. A bandage according to claim 1 in which one component of the redox catalyst is a solid reducing agent within a water-pervious coating.

5. A bandage according to claim 4 in which the reducing agent is sodium metabisulphite which has been encapsulated.

6. A bandage according to claim 1 in which the water-pervious coating is formed from an hydroxyalkyl acrylic ester polymer or copolymer.

7. A bandage according to claim 4 in which the second component of the redox catalyst system is a copper (II) compound.

8. A bandage according to claim 1 in which the amount of catalyst in association with the prepolymer is 0.1 to 10% by weight of the prepolymer.

9. A bandage according to claim 1 in which the prepolymer is derived from an aliphatic isocyanate having 3 isocyanate groups per molecule.

10. A bandage according to claim 1 in which the prepolymer contains not less than 3 acrylic ester or methacrylic ester groups and is a viscous liquid.

11. A water-activatable vinyl polymerisation redox catalyst for polymerising hydrophilic prepolymers containing not less than two polymerisable vinyl groups in which at least one component of said catalyst is in solid particulate form in a water-pervious coating in which the particles have an uncoated size of from 10 to 500 μm and in which the water-pervious coating is present over in excess of 95% of the particle surface and in which the weight ratio of catalyst to coating is 99:1 to 1:9 and in which the coating is insoluble in the prepolymer.

12. A catalyst according to claim 11 characterised in that the catalyst comprises a copper (II) salt and a reducing agent in solid form in a water-pervious coating.

13. A process for the preparation of an orthopaedic bandage which comprises coating or impregnating a support with a vinyl compound which compound polymerises when exposed to a water-activated polymerisation catalyst in which the vinyl compound is a hydrophilic prepolymer which contains more than one polymerisable vinyl group in association with at least one component of a water activatable vinyl polymerisation redox catalyst in solid particulate form in a water-pervious coating in which the particles have an uncoated size of from 10 to 500 μm and in which the water-pervious coating is present over in excess of 95% of the particle surface and in which the weight ratio of catalyst to coating is 99:1 to 1:9 and in which the coating is insoluble in the prepolymer.

14. A method of forming a rigid orthopaedic cast for body members which comprises providing an orthopaedic bandage comprising a support carrying a compound which polymerises when exposed to a water-activated vinyl polymerisation redox catalyst, providing a water activatable vinyl polymerisation catalyst, and dipping in water, wrapping the orthopaedic bandage around the member to be immobilised wherein the vinyl compound is a hydrophilic prepolymer which contains not less than two polymerisable vinyl groups in association with at least one component of the catalyst in solid particulate form in a water-pervious coating in which the particles have an uncoated size of from 10 to 500 μm and in which the water-pervious coating is present over in excess of 95% of the particle surface and in which the weight ratio of catalyst to coating is 99:1 to 1:9 and in which the coating is insoluble in the prepolymer.

15. A cast forming, water-curable composition comprising a vinyl compound which compound polymerises when exposed to a water-activated vinyl polymerisation catalyst wherein the vinyl compound is a polymerisable hydrophilic prepolymer which contains not less than two polymerisable vinyl groups and said prepolymer is in association with at least one component of a water-activatable vinyl polymerisation redox catalyst in a solid particulate form in a water pervious coating in which the particles have an uncoated size of from 10 to 500 μm and in which the water-pervious coating is present over in excess of 95% of the particle surface and in which the weight ratio of catalyst to coating is 99:1 to 1:9 and in which the coating is insoluble in the prepolymer.

16. A process for the preparation of a redox catalyst component coated in a hydroxyethyl acrylic ester polymer or copolymer, which process comprises suspending the finely divided particulate component having a particle size of 10 to 500 μm in a solution of a hydroxyethyl acryl ester optionally together with a vinylic comonomer compatible therewith in a solvent which is not a solvent for the desired comonomer, and polymerising the ester optionally together with its vinylic comonomer about the component particles to form a water-pervious coating on the particles of the component so that in excess of 95% of the particle surface is coated and the weight ratio of catalyst to coating is 99:1 to 1:9.

* * * * *